United States Patent [19]

Touitou

[11] Patent Number: 5,716,638
[45] Date of Patent: *Feb. 10, 1998

[54] COMPOSITION FOR APPLYING ACTIVE SUBSTANCES TO OR THROUGH THE SKIN

[75] Inventor: Elka Touitou, Jerusalem, Israel

[73] Assignee: Yissum Research Development Company of The Hebrew University of Jerusalem, Jerusalem, Israel

[ * ] Notice: The term of this patent shall not extend beyond the expiration date of Pat. No. 5,540,934.

[21] Appl. No.: 563,144

[22] Filed: Nov. 27, 1995

Related U.S. Application Data

[63] Continuation-in-part of Ser. No. 264,204, Jun. 22, 1994, Pat. No. 5,540,934.
[51] Int. Cl.$^6$ ............................................. A61K 9/127
[52] U.S. Cl. .................... 424/450; 424/401; 424/63; 264/4.1; 264/4.3
[58] Field of Search ............................ 424/450, 401, 424/63; 264/4.1, 4.3

[56] References Cited

U.S. PATENT DOCUMENTS

| | | | |
|---|---|---|---|
| 4,761,288 | 8/1988 | Mezei | 424/450 |
| 4,994,213 | 2/1991 | Aitcheson et al. | 264/4.6 |
| 5,004,611 | 4/1991 | Leigh | 424/450 |
| 5,077,057 | 12/1991 | Szoka, Jr. | 424/450 |
| 5,154,930 | 10/1992 | Popescu et al. | 424/489 |
| 5,540,934 | 7/1996 | Touitou | 424/450 |

OTHER PUBLICATIONS

Touitou et al., International Journal of Pharmaceutics, Modulation of Caffeine Skin . . . , 103 (1994) 131–136.
Touitou et al., Journal of Pharmaceutical Sciences, Liposomes as Carriers for . . . , vol. 83, No. 9, Sep. 1994.
Riaz et al., Riaz, Weinr, and Martin, Liposomes, Chapter 16, pp. 568–603.
Batzri et al., Single Bilayer Liposomes Prepared Without Sonication, Biochim.Biophys.Acta. 298 (1973) 1015–1019.
Kremer et al., Vesicles of Variable Diameter Prepared By Modified Injection Method, Biochemistry 16 (1977) pp. 3932–3935.
Barry, V.W. Optimizing Percutaneous Absorption. In Bronaugh, R.L. and Maibach, M.I. (Eds), Percutaneous Absorption, Dekker, New York, 1989, pp. 531–565.
Touitou et al., Altered Skin Permeation Of Highly Lipophilic Molecule: Tetrahydrocannabinol. Int. J. Pharm. 43 (1988) 17–22.
Touitou et al. Enhanced Permeation Of Theophylline Through The Skin And Its Effect On Fibroblast Proliferation. Int. J. Pharm. 70 (1991) 159–166.
Joachim Roding, Natipide II: New Easy Liposome System, Lecture held at In–Cosmetics 6–8 Mar. 1990, Birmingham.
Eugene R. Cooper, Increased Skin Permeability For Lipophilic Molecules, Journal of Pharmaceutical Sciences, vol. 73, No. 8, Aug. 1984.

*Primary Examiner*—Gollamudi S. Kishore
*Attorney, Agent, or Firm*—Evenson, McKeown, Edwards & Lenahan, PLLC

[57] ABSTRACT

A cosmetic or medical composition for topical application to the skin. It results in the transdermal passage of an active ingredient, or in the introduction of such agent into the skin. The essential components of such compositions are phospholipids, an aliphatic alcohol of three or four carbon atoms or a combination of these alcohols, water and a compatible active ingredient, optionally with propylene glycol. Compositions advantageously comprise from 0.5% to 10% phospholipids, from 5% to 35% of a $C_3$- or $C_4$-alcohol, 15 to 30% ethanol, which contain together at least 20% but not more than 40 wt. % of ethanol and the $C_3$-alcohol; up to 20 wt. % propylene glycol, at least 20% water and at least one active ingredient. The compositions are suitable for the topical application of a wide variety of cosmetic and pharmaceutically active compounds. Phospholipids of choice are phosphatidylcholine, (P C), hydrogenated P C, phosphatidic acid (P A), phosphatidylserine (P S), phosphatidylethanolamine (P E), phosphatidylglycerol (P P G) and phosphatidylinositol (P I).

5 Claims, 2 Drawing Sheets

FIG.2

COMPOSITION FOR APPLYING ACTIVE SUBSTANCES TO OR THROUGH THE SKIN

This application is a CIP of U.S. application Ser. No. 08/264,204 filed on Jun. 22, 1994, now U.S. Pat. No. 5,540,934.

FIELD OF THE INVENTION

The invention relates to novel compositions containing phospholipids, short chain alcohols (C2–C4) and water. These compositions may also contain polyols.

Preferred compositions contain phospholipid, ethanol (EtOH), water (DDW), and propylene glycol (PC).

This invention relates to pharmaceutical, cosmetic, verterinary or phytopharmaceutical compositions for delivery to skin, membranes, or tissues, which enhance the delivery of the active agent at the site of application, where the agent may form a reservoir in the skin (membrane, tissue) or may be absorbed systemically into the blood circulation.

The compositions are hydro-alcoholic or hydro/alcoholic/glycolic phospholipid systems in which the concentration of alcohols, or their combination is relatively high. The main components of these systems are: phospholipids [with various chemical structures like phosphatidylcholine (PC(), hydrogenated PC, phosphalidic acid (PA), phosphatidylserine (PS),- phosphatidylethanolamine (PE), phosphatidylglycerol (PPG), phosphatidylinositol (Pt), hydrogenated PC and others], ethanol (or other short chain alcohols), water and propylene glycol (or other glycols).

The novel composition enables the delivery of higher concentrations of active agent to/through membrane (skin). The delivery can be modulated by changes in alcohol:wager or alcohol-polyol:water ratio.

STATE OF THE PRIOR ART

In drug deliver, there are a number of enhancing agents, some used in research and some on the market, for promoting and increasing the amount of drug delivered to/through the skin. Examples of these enhancing agents are. DMSO, pyrrolidone derivatives, n-decylMSO, some surfactants, oleic acid, ethanol, Azone®, and others(Barry, 1989).

Phospholipids are known for their broad use in liposomal systems as well as emulsifiers in the preparation of emulsions. All these systems used for pharmaceutical or cosmetic proposes are aqueous systems with small if any concentration of alcohol and/or glycol for preservation and/or improving texture of the formulation. Emulsions containing phospholipids are prepared by mixing an aqueous and an oily phase, in some cases followed by use of an homogenizer.

Preparation of liposomal systems involves the use of organic solvents such as chloroform, alcohols and others. The prior art teaches away from high concentrations of alcohol in the final liposomal preparations. In some methods of preparation, an organic phospholipid solution is evaporated to form a lipidic film, which is then hydrated to give an aqueous vesicular system (Riaz et al., 1988). In alternative methods, liposomes are prepared by injecting an ethanolic solution of lipid into an aqueous solution, resulting in a dilute ethanolic solution (2.5–7.5% ethanol)(Batzri et al., 1973) or by dilution of proliposomes (Leigh, 1991). The alcohol, is then removed by different means such as dialysis (Kremer et al, 1977) or is diluted. The alcohol, if present is in low concentrations only, less than about 20% in the final product (e.g. 7.5%, Kremer et al, 1977; Leigh, 1991).

BRIEF DESCRIPTION OF THE INVENTION

The invention relates to compositions which are hydro/alcoholic or hydro/alcoholic/glycolic phospholipid systems in which the concentration of alcohol or its combination with polyol is relatively high. We call these compositions: Ethosomal systems. The systems described in this invention are pharmaceutical, cosmetic, phytopharmaceutical or veterinary compositions for application to the skin (or other tissues) comprised of combinations of phospholipids, alcohols, water and glycol (polyols), as major components. An ethosomal system is a skin permeation enhancing system which has the potential to form ethosomes, which are "soft" vesicles formed from phospholipid in the presence of water and ethanol (alcohol) and sometimes glycols (polyols). The size of the vesicles depends on the water: alcohol ratio (see Tables 3–5) and on the phospholipid concentration. On the skin, the ethosomes change their size by fusing together as a result of the change in solvent ratio. In the preparation, the vesicle size does not change since the ratio between the solvents is constant. Penetration and evaporation of the alcohol following application to the skin allows the transition from small to large vesicles, which grow in size until a film is formed.

An important characteristic of ethosomes is enhanced membrane permeability for various compounds. Ethosomal systems, vesicular in nature, depending on the ratio of the components and the chemical structure of the phospolipids, can be comprised of very small entities (nm's) up to larger vesicles (mm's) (see Tables 3–5). High alcoholic (organic solvent) concentration favors the production of ethosomes in nm's range while high aqueous and phospholipid concentrations favor the formation of large size ethosomes. As examples, formulation 509(Table 4) containing 60% organic solvent and 38% water has a mean population of tens of nm's, while formulation 510 containing 50% organic solvent and 48% water has a mean population of 1 mm. In system 509 the concentration of ethanol was 48% while in formulation 510 the ethanol concentration is only 20%. showing that the alcohol concentration is of great importance in determining vesicle size. The phospholipids which can be used are: phosphatidylcholine (PC), phosphatidylserine (PS), phosphatidic acid (PA), phosphatidylethanolamine (PE), phosphatidylglycol (PPG), hydrogenated PC and others. Some prefered phospholipids are soya phospholipids such as Phospholipon 90 (PL-90). The concentration of phospholipid ranges between about 0.5–10% w/w. Cholesterol at concentrations ranging between about 0.1–1% can also be added to the preparation. Examples of alcohols which can be used are: ethanol and isopropyl alcohol. Examples of glycols are propylene glycol and Transcutol®. The source of the phospholipids can be egg, soybean, semi-synthetics, and synthetics. Non ionic surfactants can be combined with the phospholipids in these preparations e.g. PEG-alkyl ethers (Brij-52). Cationic lipids like cocoamide, Poe alkyl amines, dodecylamine, cetrimide, and like. The concentration of alcohol (EtOH etc.) in the final product ranges from about 20–50%. The concentration of the non-aqueous phase (alcohol and glycol combination) may range between about 22 to 70%. The rest of the carrier contains water and possible additives. Vesicle formation is dependent on the water: alcohol ratio. This ratio is kept constant in the product, therefore, no changes in the entities population occur. Nevertheless, penetration and evaporation of the alcohol following application to the skin allows the transition from small vesicles to a larger ones, finally resulting in film formation. In contrast to the present state of the art where "tough" liposomes accomplished by addition of different substances like cholesterol to the phospholipids and in absence of alcohol, this invention relates to "soft" vesicles, that can be easily formed in a hydroalcoholic medium. One of the important properties of these systems is that small entities can penetrate into the skin, while larger vesicles can form a reservoir in the skin and a film on the skin surface as a result of solvent evaporation taking place after the application. These carriers can be used to deliver various active agents such as: peptides, anti-aging, tanning agents, vitamins, antiviral drugs, psoriasis treatment agents, melanin, melatonin, hormones, medicinally active components of plants such as oleoresins, volatile oils, glycosides, alkaloides, terpenes and others.

Examples of other active agents which can be used with these systems are as follows: drugs like nicotine, nitroglycerine, estradiol (or like), testosterone (or like), progesterone, nifedipine, minoxidil, tetrahydrocannabinol (THC) or other cannabinoids, xanthines, auxiolytics (diazepam and others), antiepileptic (valnoctamide and others), diclofenac (and other NSAIDs),antibiotics, corticosteroids, tocopheral, 5-FU, acyclovir, colchicine, prazosin, papaverine, miconazole nitrate, ketoconazole and other antifungals, enzymes like SOD; peptides and amino acids.

The term "Ethosomes" designates liposomal systems of the present invention, which are based on $C_2$ to $C_4$ alcohols, or on such systems based on a mixture of such and alcohol with ethanol.

METHODS

In vitro skin penetration/permeation measurements

Skill permeation experiments were carried out in our laboratory as previously described (Touitou, 1986; Touitou and Fabin, 1988).
Full thickness skill The animals used ill these investigations were hairless mice obtained from the Weizmanu Institute, Rohovot, Israel. The skin of 5–7 week old male mice was excised before the experiment, examined for integrity and cut for diffusion cell assembly. In most of the experiments, the skin from the abdominal site was used.
In vitro permeation experiments in horizontal diffusion cells.

The Valia-Chien cell assembly was used to perform the experiments on permeation of the drugs from various donor compositions through hairless mouse skin and the concentration in the skin. Mouse skin treated as described above was mounted in cells with a surface area of 0.64 cm² and half-cell volume of 3 ml. The receiver compartments contained a medium (hydroalcoholic, water, or buffer solutions) for ensuring pseudo-sink conditions. During the experiment, samples were withdrawn and mixed with scintillation cocktail (Packard, USA) and assayed in the Kontron Betamatic Scintillation Counter (Lumitron Scientific Industries) or directly assayed by HPLC. The sample volumes were replaced with fresh solution. The results were treated using the "Transderm" computer program (Touitou and Fabin, 1988). Each experiment was tetraplicated. The two-tailed, paired Wilcoxon test was used for determining the statistical significance of the effect of enhancers on the permeability coefficient changes. For these analyses, the "Balance" (IBM) computer program was used.

Skin Permeation Determination in Franz Cells

The permeation flux of drugs and the quantity of drug in the skin from the test system was measured in vertical cells (Franz diffusion cells). The experimental system conditions were: receiver temperature 370° C. and receiver volume 4–8 ml. The samples were assayed either by scintillation counting or by HPLC. The results are presented as a mean of 4 experiments and were analyzed by Transderm and by Balance (IBM) computer programs.
Size Distribution of Liposomes:

The size distribution of ethosomes was measured in a Malvern autosizer (Malvern). (See Tables3–5).
Method of Preparation and Compositions:

Examples of compositions are given in Tables 1 and 2.

a) Ethosomal system containing a relatively high concentration of Ethanol or Ethanol and Propylene Glycol was obtained as follows:

A lipophilic drug(10%) and PL-90(5%) were dissolved in an EtOH-PG(62.4%) mixture at room temperature. DDW (22.6%) was then added with vigorous stirring.

See example II—Immune agent.

b) Ethosomal systems containing a relatively high concentration of Ethanol (20–50%) or Ethanol and Propylene Glycol (22–70%) were obtained as follows:

PL-90 (0.5–10%) was dissolved in the EtOH-PG mixture. Hydrophilic drugs were dissolved in DDW and added to the PL-90 solution.

c) Ethosomal system was prepared by mixing (Heidolph mixer) PL-90 and water in concentrations as in "b" and heating to dispersion at 60°–70° C. The dispersion was then cooled (ice bath) with constant mixing for 30 minutes. To the above dispersion a solution of 2% Minoxidil in ethanol-propylene glycol (concentration as above) was added with vigorous mixing. A vesicular system was obtained. The preparation may be passed through a homogenizer (like Gasoline).

d) Minoxidil ethosomes were prepared by gently heating or at room temperature, a solution of soybean lecithin (Phospholipon 90) and Minoxidil in a propylene glycol ethanol mixture. Distilled water or buffer solution was added to the above system. A vesicular system was formed. The preparation may be passed through a homogenizer (like Gasoline). concentrations of ingredients as in "c".

e) A vesicular system containing a relatively high concentration of Ethanol or Ethanol and Propylene Glycol was obtained as follows: A dispersion containing soya phospholipid (Phospholipon 90), Minoxidil, Ethanol, propylene glycol, double distilled water or buffer solution, is passed through a homogenizer in order to reduce particle size concentrations of ingredients as in "c".

f) Composition and preparation as described in a–c but containing 0.2 % cholesterol in addition.

g) As in a–d where mixtures of phospholipids are used.

h) The vesicular systems can be incorporated in various carriers such as: PVP/VA (gels, membranes, solutions), PVP (gels, membranes, solutions) carbomer gels, polaxomer (gels, solutions), emulsions, adhesives, creams, Plutonit F127 or Tetronic gels and the like, cellulose derivatives gels, plant extract gels (aloe vera gel etc), and the like.

TABLE 1

Examples of skin permeation enhancing systems containing various drugs

| COMPONENTS | DYPH1 | DYPH2 | MND200 | SOD | Immune | THC 1 | MM33 | MM39 | MM42 | MM43 |
|---|---|---|---|---|---|---|---|---|---|---|
| DYPHYLLINE | 1% | 1% | | | | | | | | |
| ACYCLOVIR | | | | | | | | | | |
| DICLOFENAC | | | 7 μCi/ml | | | | | | | |
| SOD | | | | 6% | | | | | | |
| ROQUINIMEX | | | | | 10% | | | | | |
| MINOXIDIL | | | | | | | 2% | 2% | 2% | 2% |
| THC | | | | | | 7 μci/ml | | | | |
| PL-90 | 5% | 5% | 2% | 2% | 5% | 2% | 2% | 2% | .5% | 5% |
| CHOLESTEROL | — | — | — | — | — | — | — | — | — | 0.1% |
| PG | 18.8% | — | 19.6% | 18.4% | 31.2% | 19.6% | 19.2% | 19.2% | 19.5% | 18.6% |
| DDW | 47% | 47% | 49% | 46% | 22.6% | 29.4 | 28.8% | 48% | 48.8% | 27.9% |
| EtOH | 28.2% | 47% | 29.4% | 27.6% | 31.2% | 49% | 48% | 28.8% | 29.3% | 46.5% |

Examples of compositions and preparation methods:

| Example I-SOD ethosomal preparation | | | |
|---|---|---|---|
| A) | Amerchol L-101 | 57.1% | 4 parts |
| | Amerlate P | 14.3% | 1 part |
| | Brij 52 | 28.6% | 2 parts |
| B) | Carbopol 934P | | |
| | DDW | 98% | |
| | TEA | | |
| | SOD | 6% | |
| C1) | PL-90 | 2% | |
| | DDW | 46% | |
| C2) | EtOH 3 | 27.6% | |
| | PG | 18.4% | |

Gel preparation:

1. Preparation of "A" by melting the ingredients in a water bath. Cool while stirring.
2. Disperse Carb 934 P in DDW at room temperature.
3. Mix A and B in the ratio of 7% of A with 93% B and add TEA.

System preparation:

4. SOD was dissolved in a PL-90 dispersion in DDW [obtained by heating in a water bath of 700° C. with constant mixing (C1)].
5. An EtOH:PG mixture (C2) was prepared and added to C1 with vigorous ,nixing and cooling in an ice bath.

Final formulation:

6. Mix gel with the system in a 1:1 ratio.

| Drug | 3% |
|---|---|
| Lipid phase (A) | 3.5% |
| Gel (B) | 46.5% |
| PL-90 + DDW (C1) | 22% |
| PG + EtOH (C2) | 25% |

| Example II-IMMUNE AGENT (ROQUINIMEX) ethosomal preparation | | |
|---|---|---|
| A) | Pluronic F127 | 40% |
| | DDW | 60% |
| B) | ROQUINIMEX | 10% |
| | PL-90 | 5% |
| | EtOH 95% | 31.2% |
| | PG | 31.2% |
| | DDW | 22.6% |

Prepare a Pluronic gel of 40% in DDW. Dissolve Roquinimex and PL-90 in the EtOH-PG mixture. Add DDW to the latter with vigorous stirring.

Add B to A with vigorous stirring, at a ratio of 1:1.

| Example III-THC Ethosomal preparation | |
|---|---|
| THC | 1% |
| PL-90 | 4.2% |
| EtOH | 51.7% |
| PG | 15% |
| PVP-VA S-630 | 12.5% |
| DDW | 16.6% |

THC and PL-90 were dissolved in an EtOH-PG mixture with gentle heating while mixing. DDW was added with continuous stirring. PVP-VA was slowly added while stirring. The preparation was sonicated in 3 cycles of 5 minutes with 5 minutes rest between each cycle.

| Example IV-Minoxidil ethosomal preparation (MM50-G) | | |
|---|---|---|
| A) | Carbopol 934P | 0.75% |
| | Ethomeen C/15 | 0.75% |
| | DDW | 73.5% |
| | EtOH | 25% |
| B) | Minoxidil | 4% |
| | PL-90 | 5% |
| | EtOH 95% | 40% |
| | PG | 20% |
| | DDW | 31% |
| | Tocopherol | 0.02% |
| MM50-G, Final concentrations: | | |
| Carbopol 934P | | 0.38% |
| Ethomeen C/15 | | 0.38% |
| Minoxidil | | 2% |
| PL-90 | | 2.5% |
| EtOH (95%) | | 32.5% |
| PG | | 10% |
| DDW | | 52.3% |

Carbopol gel was prepared by dispersing Carbopol 934P in DDW and Ethomeen was added. Ethanol was added to obtain an hydroalcoholic gel. The drug, antioxidant, and PL-90 were dissolved in the EtOH -PG mixture with gentle heating (30° C.). DDW was added with vigorous stirring to obtain the system.

The system may be homogenized.

B was added to A at a 1:1 ratio.

The mean size of vesicles was found to be 35 nm

Example V—Minoxidil ethosomal preparation (MM)

As in example IV (MM50-G) with the following variations:

The gel:system ratio may be changed to 1:2, 1:3, or 1:4.

The ratio between solvents can be changed: EtOH (25–49%), PG (0–20%), and DDW (25–49%)can be changed.

The PL-90 concentration can be raised to about 10%.

| Example VI-DICLOFENAC SODIUM ethosomal preparation | |
|---|---|
| Diclofenac sod. | 1% |
| PL-90 | 1% |
| Carbopol 934 | 0.9% |
| Ammonium 10% soln. | 1.8% |
| EtOH | 21.9% |
| DDW | 68.9% |
| PG | 4.16% |
| Example VII-ACYCLOVIR ethosomal preparation | |
| Acyclovir | 5% |
| Ammonium 10% soln. | 1.66% |
| Carbopol 934 | 0.83% |
| PL-90 | 2.5% |
| DDW | 58.3% |
| EtOH | 27.5% |
| PG | 4.16% |

TABLE 2

Other Examples

| Sys. No. | PL-90 | DDW | EtOH | PG | Other | Method* |
|---|---|---|---|---|---|---|
| 500 | 2 | 48 | 30 | 20 | | Hot |
| 501 | 2 | 48 | 30 | 20 | | Cold |
| 502 | 2 | 30 | 48 | 20 | | Hot |
| 503 | 2 | 30 | 48 | 20 | | Cold |
| 504 | 5 | 45 | 30 | 20 | | Hot |
| 505 | 5 | 45 | 30 | 20 | | Cold |
| 506 | 5 | 30 | 45 | 20 | | Hot |
| 507 | 5 | 30 | 45 | 20 | | Cold |
| 508 | 2 | 30 | 38 | 30 | | Cold |
| 509 | 2 | 38 | 30 | 30 | | Cold |
| 510 | 2 | 48 | 20 | 30 | | Cold |
| 511 | 1.8 | 30 | 38 | 30 | 0.2 (M(−)*) | Cold |
| 512 | 5 | 30 | 45 | 20 | | Cold |
| 513 | 5 | 35 | 30 | 30 | | Cold |
| 514 | 2 | 33 | 30 | 30 | 5 (Brij 52) | Cold |
| 515 | 17 | 26 | 40 | 17 | | Cold |
| 516 | 9.3 | 44.4 | 27.7 | 18.5 | | Cold |
| 517 | 5 | 20 | 40 | 40 | 5 (Brij 52) | Cold |
| 518 | 2 | 47 | 30 | 20 | 1 (Col**) | Cold |

TABLE 2-continued

Other Examples

Ingredients, % w/w

| Sys. No. | PL-90 | DDW | EtOH | PG | Other | Method* |
|---|---|---|---|---|---|---|
| 525 | 10 | 64 | 26 | 0 | | Hot |
| 529 | 1.7 | 55.4 | 34.3 | 8.6 | | Cold |

PL-90: phospholipid; DDW: water; Etoh: ethanol; PG: propylene glycol
*M(−): I-Menthol
**Col: Colchicine
*See "Hot" or "Cold" methods described below.

"Cold" method:

Phospholipid is dissolved in ethanol at room temperature by vigorous stirring with the use of Heidolph mixer. Propylene glycol is added during the stirring. The mixture is heated to 30° C. in a water bath. The water heated to 30° C. in a separate vessel is added to the mixture which is then stirred for 5 minutes in a covered vessel.

"Hot" method:

The phospholipid is dispersed in water by heating in a water bath at 40° C. until a colloidal solution is obtained. In a separate vessel ethanol and propylene glycol are mixed and heated to 40° C. Once both mixtures reach 40° C. the organic phase is added to the aqueous one.

During the preparation process the drug is dissolved in water or in ethanol depending on its hydrophilic/hydrophobic properties.

EXAMPLES OF SKIN PERMEATION PARAMETERS OF VARIOUS DRUGS FROM THESE SYSTEMS ($Kp$= permeability coefficient; $Qs$=quantity of drug in the skin at the end of the experiment)

Kp reflects the permeation through the skin and Qs reflects the reservoir formation in the skin.

| Example VII | |
|---|---|
| MM33 = MM36 (see Table 1) | vs blank MM (Minoxitrim ®, Trima, Israel) (2% minoxidil) |
| $Kp = 1.36 \times 10^{-2}$ cm*hr$^{-1}$ | $8.84 \times 10^{-4}$ cm*hr$^{-1}$ |
| $Qskin = 0.658$ mg/cm$^2$ | 0.0479 mg/cm$^2$ |

The ethosomal system showed an increase of 15.4 times in Kp and 13.7 times in Qs.

| Example IX | |
|---|---|
| MM39 (see Table 1) | MM blank (as above) |
| $Kp = 1.96 \times 10^{-3}$ cm*hr$^{-1}$ | $5.75 \times 10^{-5}$ cm*hr$^{-1}$ |
| $Qskin = 0.138$ mg/cm$^2$ | 0.0378 mg/cm$^2$ |

The ethosomal system showed an increase of 34 times in Kp and 3.7 times in Qs.

| THC (as in ex. III) | THC in PG:EtOH (1:1) |
|---|---|
| $Kp = 7.2 \times 10^{-3}$ cm*hr$^{-1}$ | $2.03 \times 10^{-3}$ cm*hr$^{-1}$ |

The ethosomal system showed an increase of 3.5 times in Kp. No significant changes in other kinetic parameters were observed

Example XI

| MM50G (as in ex. IV) | MM blank |
|---|---|
| Qreceiver = 0.135 µg/cm² | 0.023 µg/cm² |

The ethosomal system showed an increase of 5.9 times in Kp

Example XII

| | ACV11 (as in ex VII) | Zovirax ® |
|---|---|---|
| Qreceiver (6 hours) | 2.9 ± 1.57 µg/cm² | 3.065 ± 0.38 µg/cm² |
| Qskin | 81.35 ± 5.58 µg/cm² | 18.35 ± 8.56 µg/cm² |

The ethosomal system showed no significant change in Kp and an increase of 4.4 times in Qs.

Example XIII

| MM122 | MM122 blank a | MM122 blank b |
|---|---|---|
| 2% PL-90, 2% Minoxidil 48% EtOH 95, 25% DDW, 20% PG | 2% PL-90, 2% Minoxidil in EtOH | 2% Minoxidil in EtOH |
| Qrec = 3672 ± 378 µg/cm² (24 hours) | 217.5 ± 118.5 µg/cm² | 66.9 ± 22.1 µg/cm² |
| Qskin = 570 ± 130.5 µg/cm² | 139.1 ± 25.3 µg/cm² | 53.5 ± 12 µg/cm² |

The ethosomal system showed an increase of 17 times in Kp and 4.1 times in Qs relative to a 2% phospholipid solution in ethanol (blank a) and an increase of 55 times in Kp and 11 times in Qs relative to an ethanolic solution (blank b). These results clearly indicate that the ethosomal system is a much more effective penetration enhancing system than ethanol or an ethanolic solution of phospholipid.

Example XIV

| | MND200 | Blank MND (only solvents) |
|---|---|---|
| Kp = | 4.27 × 10⁻³ cm*hr⁻¹ | 1.57 × 10⁻³ cm*hr⁻¹ |
| Qskin = | 2.75 × 10⁻⁵ mg/cm² | 2.35 × 10⁻⁵ mg/cm² |
| lag time = | 0:41 hrs | 2:30 hrs |

The ethosomal system showed an increase of 2.7 times in Kp no significant change in Qs and a decrease of 5 times in lag time.

Example XV

Figure 1:
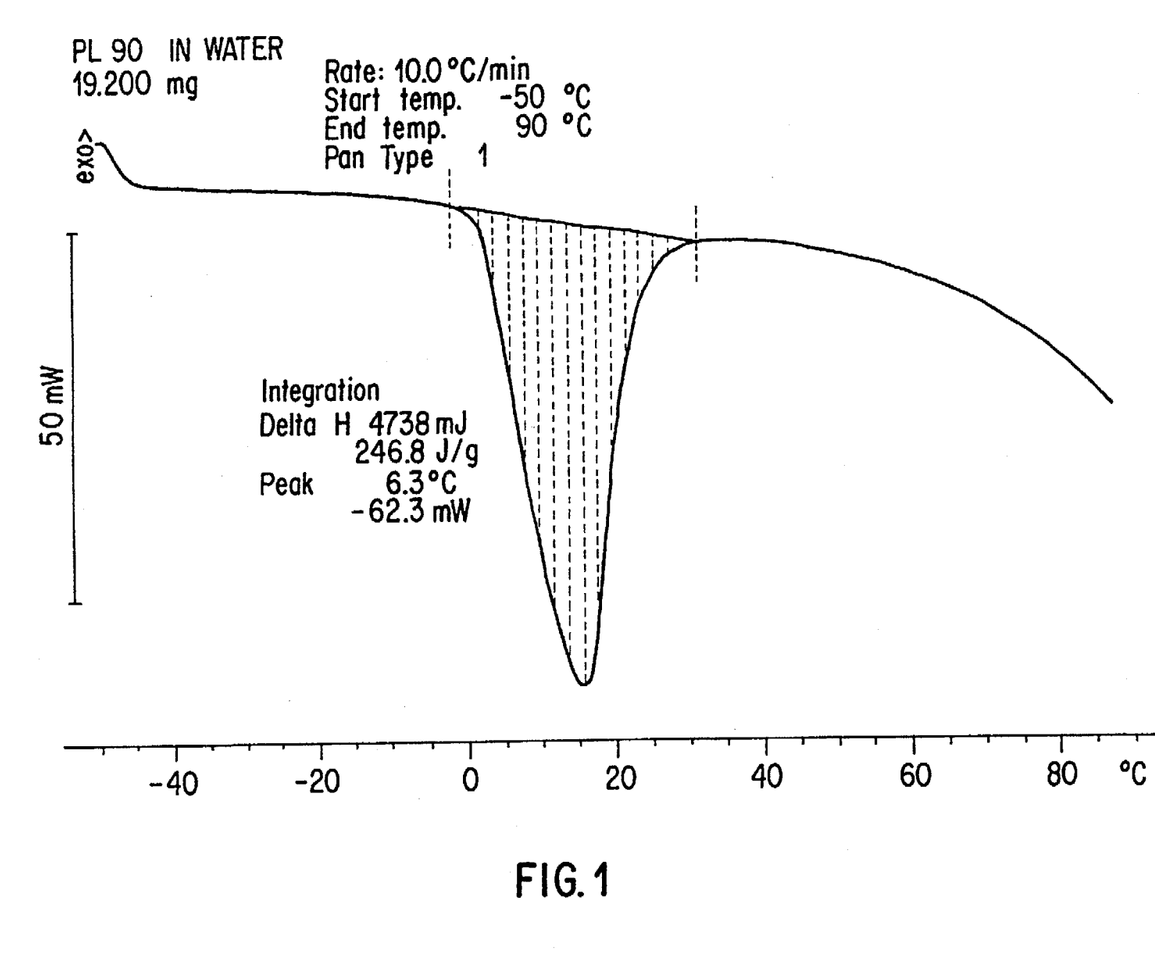
FIG. 1 is a graph showing Differential Scanning Calorimetric data of an ethosomal system containing 5% PL-90 in water.
Figure 2:
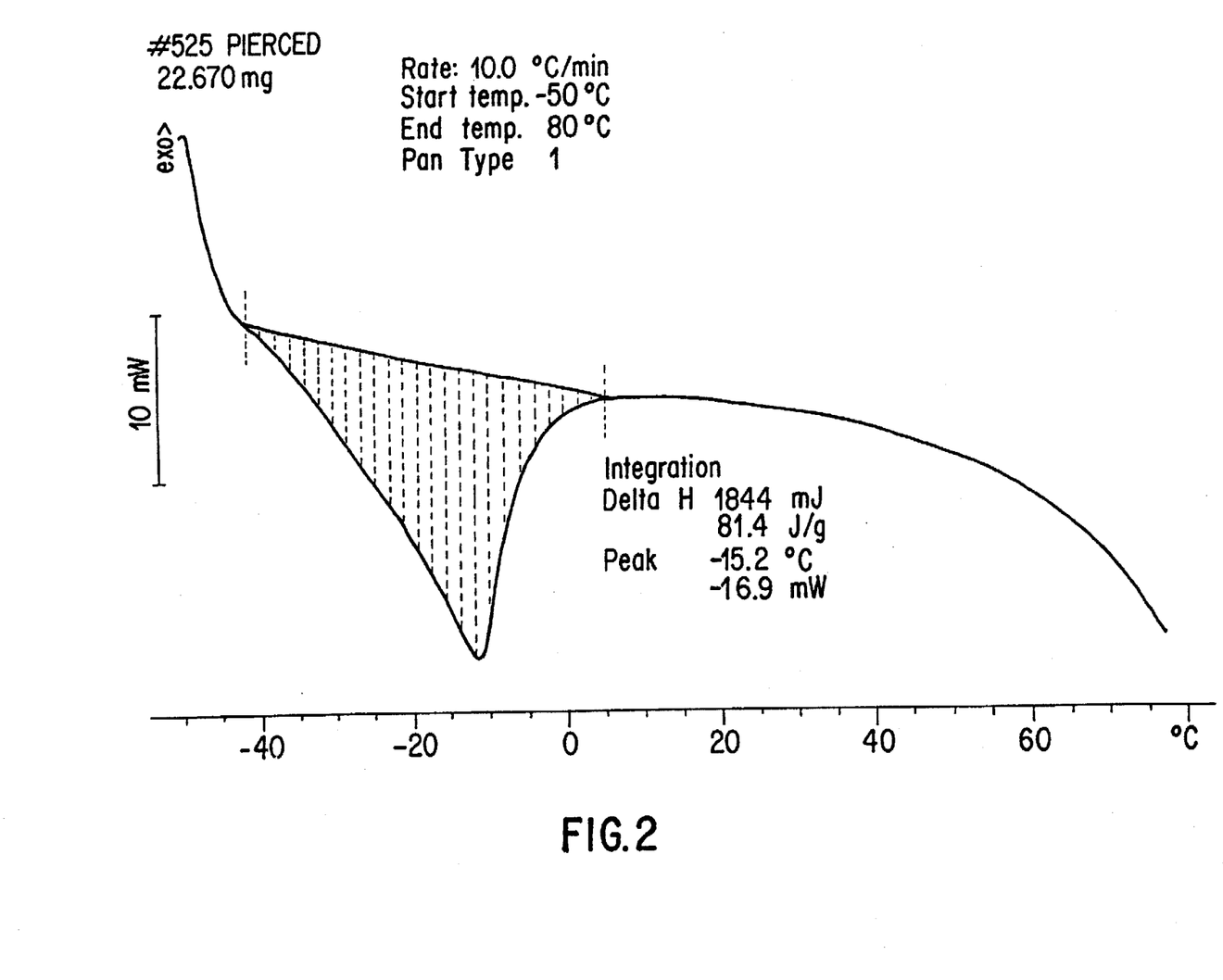
FIG. 2 is a graph showing Differential Scanning Calorimetric data of ethosomal system No. 525 (See Table 2).

Differential Scanning Calorimetric (DSC) data on a system containing 5% PL-90 in water and an ethosomal system No. 525 (see Table 2 for exact composition) are presented in FIGS. 1 and 2, respectively. The thermograms clearly show a decrease in Tin (transition temperature) value for the ethosomal system which indicates an increase in phospholipid vesicle's fluidity.

Example XVI

There were prepared: Caffeine ethosomes (liposomal systems containing 20.9 and ;35% ethanol) versus Caffeine liposomes with 5% ethanol.

All three preparations contain the same concentration of caffeine (3%) and the same phospholipid (Phospholipon 90) at 5% concentration, without propylene glycol.

Methods

In vitro skin penetration/permeation measurements. Skin permeation experiment was carried out in our laboratory by using the Valia-Chien cell assembly to perform the experiment.

The skin of 5-7 week old male mice was used in this investigation (nude mice obtained from the Weizmann Institute, Rohovot, Israel.). The skin was examined for integrity and cut for mounting on diffusion cell assembly. The skin from the back site was used.

The skin was mounted in cells with a surface area of 0.64 cm² and half-cell volume of 3 ml. The receiver compartments contained water for ensuring pseudo-sink conditions. Samples were directly assayed by HPLC (Touitou et al, 1994). The experiment was run for 24 hours. Each formulation was tested in three cells.

| Caffeine Ethosomes | |
|---|---|
| A) Caffeine | 3.0% |
| Sod. Salicylate | 4.8% |
| Distilled Water | 52.2% |
| B) Phospholipon-90 | 5.0% |
| Ethanol | 35.0% |

Example XVII

A composition was prepared as set out on page 6, b.

A) Dissolve Caffeine and Sod. Salicylate in the water.

B) Dissolve the phospholipid in ethanol. Add A to B with vigorous stirring.

| Caffeine Liposomes | |
|---|---|
| Caffeine | 3.0% |
| Sod. Salicylate | 4.8% |
| Phospholipon-90 | 5.0% |
| Ethanol | 5% |
| Distilled Water | 82.2% |

Preparation as above.

Results $Q_{rec}$=quantity of drug in the receiver compartment of the diffusion cell at the end of the experiment.

| Caffeine Lipsomes (5% ethanol) | Caffeine Ethosomes (20.9% ethanol) | Caffeine Ethosomes (35% ethanol) |
|---|---|---|
| 86.8 ± 17.1 µg/cm² | 496.6 ± 71 µg/cm² | 4794.3 ± 812 µg/cm² |

These results clearly indicate that the ethosomal system according to the invention containing 35% ethanol enabled an enhanced delivery of caffeine through the skin of 53 times higher than the liposomes containing caffeine with 5% ethanol. The above proves the outstanding improvement resulting from a high content of alcohol in the liposomal system, in the presence of liposomes.

An increase of skin penetration from 87 µg/cm2to about 4794 µg/cm², i.e., an increase by a factor of about 53 times as large, demonstrates a dramatic and unexpected result of the novel liposomes with a high ethanol content, termed "ethosomes". A 53-fold skin penetration could not be expected at all on the basis of the prior art, which clearly teaches away from the present invention, i.e. that a high ethanol content is detrimental for liposomal preparations, and that the ethanol content of the final liposome preparation ought to be reduced so as to remove a large part of the initial ethanol content or by dilution.

Example XVII

Further experiments were carried out with Minoxidil, comparing liposomes with a high ethanol content with Minoxidil in the vehicle.

The experiments were carried out as follows: The formulations tested were: Minoxidil ethosomes (liposomal systems containing ethanol) versus Minoxidil in vehicle. Both preparations contain the same concentration of Minoxidil (1%).

Methods

In vitro skin permeation measurements: Skin permeation experiment was carried out in our laboratory by using the Franz cell assembly to perform the experiment.

Frozen back side skin of a 5–7 week old male mice was used in this investigation (nude mice obtained from the Weizmann Institute, Rohovot, Israel). The skin was examined for integrity and cut for mounting on diffusion cell assembly.

Nude mouse skin was mounted in cells with a surface area of 1.77 cm² and receiver volume of about 7 ml. The receiver compartments contained 1/150 M pH7 phosphate buffer for ensuring pseudo sink conditions. Samples were directly assayed by HPLC. The experiment was run for 12 hours. Each formulation was tested in three cells.

| Minoxidil Ethosomes | |
|---|---|
| Minoxidil | 1% |
| Phospholipon | 2% |
| Ethanol 95% | 40% |
| Distilled Water | 57% |
| Minoxidil vehicle | |
| Minoxidil | 1% |
| Ethanol 95% | 40% |
| Distilled Water | 59% |

Results $Q_{rec}$=quantity in the receiver compartment of the diffusion cell at the end of experiment.

| $Q_{rec}$ | |
|---|---|
| Minoxidil vehicle | Minoxidil ethosomes |
| 16.26 ± 2.8 µg/cm² | 64.02 ± 22.5 µg/cm² |

The above results, of about 16 µg/cm² versus about 64 pg/cm² skin penetration of the two preparations, demonstrates that the "ethosomes" of the invention resulted in an about 4-fold skin penetration compared with the penetration of the active substance in the vehicle only, i.e. not in liposome form. These ethosomes were without propylene glycol.

Example XIX

The following experimental results, relate to various liposome systems of the invention containing 1% sodium diclofenac as model drug and in which various compositional factors have been changed: 1. the concentration of alcohol 2. the phospholipid 3. the type of alcohol. The results demonstrate: 1. the cruciality of high concentrations of alcohol, and that the high skin permeation from ethosomal systems of the invention is still obtained: 2. with an additional example of phospholipid (Lipold E 75-containing phosphatidyl ethanolamine and phosphatidyl choline isolated from egg, produced by Lipold KG; Germany, 3, with isopropyl alcohol, Methods:

In vitro skin permeation measurements. Skin permeation experiment was carried out in our laboratory by using the Valia Chien assembly to perform the experiments.

Frozen back side skin of a 5–7 week old mouse was used in these experiments (nude mice obtained from the Weizman Institute, Rohovot, Israel). The skin was examined for integrity and cut for mounting on diffusion cell assembly.

The skin was mounted in cells with a surface area of 0.64 cm² and receiver volume of about 3 ml. The receiver compartments contained 4/150M pH7 phosphate buffer for ensuring pseudo sink conditions.

Samples were directly assayed by HPLC. The experiments were run for 17 hours. Each formulation was tested in triplicates.

| | FORMULATIONS: | | | | | |
|---|---|---|---|---|---|---|
| | XA | XB₁ | XB₂ | XC | XD | XE |
| Sod. Diclofenac | 1 | 1 | 1 | 1 | 1 | 1 |
| Phospholipon 90 | 5 | 5 | 5 | — | — | 5 |
| Lipoid E | — | — | — | 5 | 5 | — |
| Ethanol | 5 | 21 | 35 | 5 | 35 | — |
| Isopropyl Alcohol | — | — | — | — | — | 35 |
| Distilled Water | 89 | 73 | 59 | 89 | 59 | 59 |

Results:

$Q_{rec}$=quantity in the receiver compartment of the diffusion cell at the end of experiment.

| $Q_{rec}$, µg/cm² | | | | | |
|---|---|---|---|---|---|
| XA | XB₁ | XB₂ | XC | XD | XE |
| 37.7 ± 11 | 144.1 ± 14 | 309.2 ± 29 | 57.6 ± 25 | 285.2 ± 37 | 1558.8 ± 778 |

These results clearly indicate that:

1. The ethosomal systems of the hydrophilic drug diclofenac sodium, containing a high concentration of ethanol (35%), give an enhanced delivery or drug through the skin of eight times higher than the preparation containing only 5% ethanol;
2. The enhancing effect is also obtained with isopropyl alcohol;
3. The enhancing effect is obtained when the composition or phospholipids is changed;

The above results demonstrate the improvement in permeation with novel liposimal ("Ethosomal") systems of the invention. Remark: all these systems are without propylene glycol (PG) showing the noncriticality of PG.

A BRIEF DESCRIPTION OF THE DRAWINGS

The invention is illustrated with reference to the enclosed Figures and photos, in which.

TABLE NO. 3

MALVERN AUTOSIZER II c for ethosomal system No. 501 (see Table 2)
Sample: 501; Vortex t = 22.6; Aperture: 200
Data from accumulation file sum of 5 blocks
Temperature: 22.6° C.; Viscosity: 4.1800; Refractive Index: 1.365;
Angle: 90.0

| Particle size distribution (nm.) | Graph of Distribution of mass |
|---|---|
| 10.0–12.1 | + |
| 12.1–14.6 | + |
| 14.6–17.7 | + |
| 17.7–21.5 | + |
| 21.5–26.0 | + |
| 26.0–31.5 | + |
| 31.5–38.2 | + |
| 38.2–46.2 | + |
| 46.2–56.0 | + |
| 56.0–67.9 | + |
| 67.9–82.2 | + |
| 82.2–99.6 | + |
| 99.6–120.7 | + |
| 120.7–146.3 | + |
| 146.3–177.2 | + |
| 177.2–214.7 | —+ |
| 214.7–260.1 | ———+ |
| 260.1–315.1 | —————+ |
| 315.1–381.7 | ———————————+ |
| 381.7–462.5 | ———————————————————+ |
| 462.5–560.3 | ——————————————————————+ |
| 560.3–678.8 | ——————————————+ |
| 678.8–822.4 | ————————+ |
| 822.4–996.4 | ——————+ |

TABLE NO. 4

MALVERN AUTOSIZER II c for ethosomal system No. 509 (see Table 2)
Sample: 509; Vortex + US; Non diluted
Data from accumulation file sum of 8 blocks
Temperature: 22.6° C.; Viscosity: 4.8200; Refractive Index: 1.376;
Angle: 90.0

| Particle size distribution (nm.) | Graph of Distribution of mass |
|---|---|
| 4.5–5.4 | + |
| 5.4–6.4 | ———————————————+ |
| 6.4–7.7 | ———————————————————————+ |
| 7.7–9.2 | ————————————————————————————+ |
| 9.2–11.0 | —————————————————————————————+ |
| 11.0–13.2 | ————————————————————————————+ |
| 13.2–15.8 | ——————————————————————+ |
| 15.8–18.9 | ————————————————+ |
| 18.9–22.6 | ——————————————+ |
| 22.6–27.1 | ———————————+ |
| 27.1–32.4 | ————————+ |
| 32.4–38.8 | ——————+ |
| 38.8–46.4 | ————+ |
| 46.4–55.6 | ———+ |
| 55.6–66.6 | ——+ |
| 66.6–79.7 | —+ |
| 79.7–95.5 | + |
| 95.5–114.3 | + |
| 114.3–136.8 | + |
| 136.8–163.8 | + |
| 163.8–196.2 | + |
| 196.2–234.9 | + |
| 234.9–281.2 | + |
| 281.2–336.7 | + |

TABLE NO. 5

MALVERN AUTOSIZER II c for ethosomal system No. 510 (see Table 2)
Sample: 510; Vortex + US; Non diluted
Data from accumulation file sum of 6 blocks
Temperature: 22.6° C.; Viscosity: 4.6400; Refractive Index: 1.374;
Angle: 90.0

Particle size distribution (nm.) Graph of Distribution of mass

| Size (nm) | Distribution |
|---|---|
| 17.4–21.1 | + |
| 21.1–25.6 | + |
| 25.6–31.0 | + |
| 31.0–37.6 | + |
| 37.6–45.5 | —————————————————————————————————+ |
| 45.5–55.1 | ——————————————————————+ |
| 55.1–66.8 | + |
| 66.8–80.9 | + |
| 80.9–98.0 | + |
| 98.0–118.8 | + |
| 118.8–143.9 | + |
| 143.9–174.3 | + |
| 174.3–211.2 | + |
| 211.2–255.9 | —+ |
| 255.9–310.0 | + |
| 310.0–375.6 | + |
| 375.6–455.0 | ——————————+ |
| 455.0–551.3 | ————————————+ |
| 551.3–667.9 | ————————————+ |
| 667.9–809.2 | ———————————————+ |
| 809.2–980.3 | ——————————————————+ |
| 980.3–1187.7 | ——————————————————+ |
| 1187.7–1438.9 | ———————————————+ |
| 1438.9–1743.3 | ———————————+ |

METHODS

In vitro skin penetration/permeation measurements
Full thickness skin

The animals used in these investigations were hairless mice obtained from the Weizmann Institute, Rohovot, Israel. The skin of 5–7 week old male mice was excised before the experiment, examined for integrity and cut for diffusion cell assembly. In most of the experiments, the skin from the abdominal site was used.

In vitro permeation experiments in horizontal diffusion cells:

The Valia-Chien cell assembly was used to perform the experiments on permeation of the drugs front various donor compositions through hairless mouse skin and the concentration in the skin. Mouse skin treated as described above was mounted in cells with a surface area of 0.64 cm$^2$ and half-cell volume of 3 ml. The receiver compartments contained a medium (hydroalcoholic, water, or buffer solutions) for ensuring pseudo-sink conditions. During the experiment, samples were withdrawn and assayed by HPLC. The sample volumes were replaced with fresh solution. Each experiment was triplicated.

Size Distribution of Liposomes:

The size distribution of ethosomes was measured in a Malvern autosizer (Malvern) (See Tables 6 to 12).

TABLE 6

| | Formulation | | | | |
|---|---|---|---|---|---|
| | 5001 | 5005 | 5011 % | 5012 | 5013 |
| Phospholipon 90 | 5 | 5 | 5 | 5 | 5 |
| Isopropyl alcohol | 35 | 21 | 15 | 5 | 5 |

TABLE 6-continued

| | Formulation | | | | |
|---|---|---|---|---|---|
| | 5001 | 5005 | 5011 % | 5012 | 5013 |
| Propylene glycol | | | | | 5 |
| DDW | 60 | 74 | 80 | 90 | 85 |

TABLE 7

Example - Ethosomal preparations with isopropyl alcohol

| | IP1 | IP2 | IP3 | IP4 | IP5 | IP6 | IP7 |
|---|---|---|---|---|---|---|---|
| | % w/w | | | | | | |
| THC | | | | | | | 0.1 |
| Minoxidil | 1 | 1 | 1 | 1 | | | |
| Phospholipon-90 | 5 | 5 | 10 | 5 | 2 | 5 | 5 |
| Isopropyl alcohol | 24 | 21 | 35 | 10 | 20 | 5 | 35 |
| Ethanol | 15 | | | 25 | | 30 | |
| DDW | 53 | 73 | 49 | 60 | 78 | 60 | 54 |
| PG | 2 | | 5 | | | | 5 |

Example - Acyclovir ethosomal preparations with isopropyl alcohol

| | | | |
|---|---|---|---|
| Acyclovir | 1% | 5% | 5% |
| Ammonium 10% soln. | 1.7% | 1.8% | 1.8 |
| Carbopol 934 | 1% | 0.8% | 0.8% |
| PL-90 | 2.5% | 3% | 2.5% |
| DDW | 58.8% | 64.4% | 59.9% |
| EtOH | 25% | | 25% |
| Isopropyl alcohol | 10% | 25% | 5% |

EXAMPLES OF SKIN PERMEATION PARAMETERS FROM ETHOSOMAL SYSTEMS

Qs=quantity of drug in the skin at the end of the experiment,

Qr=quantity of drug in the receiver end the end of the experiment, Qr reflects the permeation through the skin and Qs reflects the drug reservoir formation in the skin.

TABLE 8

5001

Particle size distribution (nm.) Graph of Intensity distribution

| Size Class | % by Intensity | | | % by mass | | | % by number | | |
|---|---|---|---|---|---|---|---|---|---|
| | Under | In | Above | Under | In | Above | Under | In | Above |
| 13.4–16.3 | 0.0 | 0.0 | 100.0 | 0.0 | 0.0 | 100.0 | 0.0 | 0.0 | 100.0 |
| 16.3–19.7 | 0.0 | 0.0 | 100.0 | 0.0 | 0.0 | 100.0 | 0.0 | 0.0 | 100.0 |
| 19.7–23.9 | 0.0 | 0.0 | 100.0 | 0.0 | 0.0 | 100.0 | 0.0 | 0.0 | 100.0 |
| 23.9–28.9 | 0.0 | 0.0 | 100.0 | 0.0 | 0.0 | 100.0 | 0.0 | 0.0 | 100.0 |
| 28.9–35.0 | 0.0 | 0.0 | 100.0 | 0.0 | 0.0 | 100.0 | 0.0 | 0.0 | 100.0 |
| 35.0–42.4 | 0.0 | 0.0 | 100.0 | 0.0 | 0.0 | 100.0 | 0.0 | 0.0 | 100.0 |
| 42.4–51.4 | 0.0 | 0.0 | 100.0 | 0.0 | 0.0 | 100.0 | 0.0 | 0.0 | 100.0 |
| 51.4–62.3 | 0.0 | 0.0 | 100.0 | 0.0 | 0.0 | 100.0 | 0.0 | 0.0 | 100.0 |
| 62.3–75.5 | 0.0 | 0.0 | 100.0 | 0.0 | 0.0 | 100.0 | 0.0 | 0.0 | 100.0 |
| 75.5–91.4 | 0.0 | 0.0 | 100.0 | 0.0 | 0.0 | 100.0 | 0.0 | 0.0 | 100.0 |
| 91.4–110.8 | 0.0 | 0.0 | 100.0 | 0.0 | 0.0 | 100.0 | 0.0 | 0.0 | 100.0 |
| 110.8–134.2 | 0.0 | 0.0 | 100.0 | 0.0 | 0.0 | 100.0 | 0.0 | 0.0 | 100.0 |
| 134.2–162.6 | 0.0 | 0.0 | 100.0 | 0.0 | 0.0 | 100.0 | 0.0 | 0.0 | 100.0 |
| 162.6–197.0 | 0.0 | 2.6 | 97.4 | 0.0 | 0.1 | 99.9 | 0.0 | 3.0 | 97.0 |
| 197.0–238.8 | 2.8 | 4.0 | 93.4 | 0.1 | 0.2 | 99.7 | 3.0 | 2.6 | 94.5 |
| 238.8–289.1 | 6.5 | 5.6 | 87.8 | 0.3 | 0.3 | 99.4 | 5.5 | 1.9 | 92.5 |
| 289.1–350.3 | 12.2 | 7.4 | 80.4 | 0.6 | 0.6 | 98.8 | 7.5 | 2.2 | 90.3 |
| 350.3–424.4 | 19.6 | 9.4 | 71.0 | 1.2 | 14.7 | 84.2 | 9.7 | 33.4 | 56.8 |
| 424.4–514.2 | 29.0 | 11.6 | 59.4 | 15.8 | 28.8 | 55.4 | 43.2 | 36.9 | 19.9 |
| 514.2–622.9 | 40.8 | 12.2 | 47.2 | 44.6 | 15.5 | 39.9 | 80.1 | 11.2 | 8.8 |
| 622.9–754.7 | 52.8 | 12.5 | 34.7 | 60.1 | 8.7 | 31.2 | 91.2 | 3.5 | 5.2 |
| 754.7–914.3 | 65.3 | 11.9 | 22.8 | 68.8 | 15.5 | 15.7 | 94.8 | 3.5 | 1.7 |
| 914.3–1107.7 | 77.2 | 10.9 | 12.0 | 84.3 | 10.0 | 5.6 | 98.3 | 1.3 | 0.4 |
| 1107.7–1342.0 | 88.0 | 12.0 | 0.0 | 94.4 | 5.6 | 0.0 | 99.6 | 0.4 | 0.0 |

TABLE 9

5005

Particle size distribution (nm.) Graph of Intensity distribution

TABLE 9-continued

5005

| Size range | Graph |
|---|---|
| 94.1–114.1 | |
| 114.1–138.2 | |
| 138.2–167.4 | |
| 167.4–202.8 | |
| 202.8–245.7 | |
| 245.7–297.7 | |
| 297.7–360.7 | |
| 360.7–437.0 | |
| 437.0–529.4 | |
| 529.4–641.4 | |
| 641.4–777.1 | |
| 777.1–941.5 | |
| 941.5–1140.6 | |
| 1140.6–1381.9 | |
| 1381.9–1674.2 | |

| | % by Intensity | | | % by mass | | | % by number | | |
|---|---|---|---|---|---|---|---|---|---|
| Size Class | Under | In | Above | Under | In | Above | Under | In | Above |
| 16.7–20.3 | 0.0 | 0.0 | 100.0 | 0.0 | 0.0 | 100.0 | 0.0 | 0.0 | 100.0 |
| 20.3–24.6 | 0.0 | 0.0 | 100.0 | 0.0 | 0.0 | 100.0 | 0.0 | 0.0 | 100.0 |
| 24.6–29.8 | 0.0 | 0.0 | 100.0 | 0.0 | 0.0 | 100.0 | 0.0 | 0.0 | 100.0 |
| 29.8–36.1 | 0.0 | 0.0 | 100.0 | 0.0 | 0.0 | 100.0 | 0.0 | 0.0 | 100.0 |
| 36.1–43.7 | 0.0 | 0.0 | 100.0 | 0.0 | 0.0 | 100.0 | 0.0 | 0.0 | 100.0 |
| 43.7–52.9 | 0.0 | 0.0 | 100.0 | 0.0 | 0.0 | 100.0 | 0.0 | 0.0 | 100.0 |
| 52.9–64.1 | 0.0 | 0.0 | 100.0 | 0.0 | 0.0 | 100.0 | 0.0 | 0.0 | 100.0 |
| 64.1–77.7 | 0.0 | 0.0 | 100.0 | 0.0 | 0.0 | 100.0 | 0.0 | 0.0 | 100.0 |
| 77.7–94.1 | 0.0 | 0.0 | 100.0 | 0.0 | 0.0 | 100.0 | 0.0 | 0.0 | 100.0 |
| 94.1–114.1 | 0.0 | 2.7 | 97.3 | 0.0 | 0.4 | 99.6 | 0.0 | 24.2 | 75.8 |
| 114.1–138.2 | 2.7 | 3.2 | 94.1 | 0.4 | 0.4 | 99.2 | 24.2 | 12.4 | 63.4 |
| 138.2–167.4 | 5.9 | 0.0 | 94.1 | 0.8 | 0.0 | 99.2 | 36.6 | 0.0 | 63.4 |
| 167.4–202.8 | 5.9 | 3.2 | 90.9 | 0.8 | 0.2 | 99.0 | 36.6 | 2.0 | 61.4 |
| 202.8–245.7 | 9.1 | 7.2 | 83.6 | 1.0 | 0.4 | 98.6 | 38.6 | 2.3 | 59.1 |
| 245.7–297.7 | 16.4 | 14.7 | 68.9 | 1.4 | 0.5 | 98.1 | 40.9 | 1.7 | 57.4 |
| 297.7–360.7 | 31.1 | 7.2 | 61.7 | 1.9 | 0.9 | 97.2 | 42.6 | 1.7 | 55.7 |
| 360.7–437.0 | 38.3 | 13.7 | 47.9 | 2.8 | 21.5 | 75.7 | 44.3 | 22.7 | 33.0 |
| 437.0–529.4 | 52.1 | 14.0 | 33.9 | 24.3 | 41.7 | 34.0 | 67.0 | 24.7 | 8.4 |
| 529.4–641.4 | 66.1 | 11.4 | 22.6 | 66.0 | 21.6 | 12.4 | 91.6 | 7.2 | 1.2 |
| 641.4–777.1 | 77.4 | 8.4 | 14.2 | 87.6 | 2.8 | 9.6 | 98.8 | 0.5 | 0.6 |
| 777.1–941.5 | 85.8 | 6.0 | 8.1 | 90.4 | 4.0 | 5.6 | 99.4 | 0.4 | 0.2 |
| 941.5–1140.6 | 91.9 | 4.1 | 4.0 | 94.4 | 2.4 | 3.2 | 99.8 | 0.1 | 0.1 |
| 1140.6–1381.9 | 96.0 | 2.5 | 1.5 | 96.8 | 1.3 | 1.9 | 99.9 | 0.0 | 0.0 |
| 1381.9–1674.2 | 98.5 | 1.5 | 0.0 | 98.1 | 1.9 | 0.0 | 100.0 | 0.0 | 0.0 |

TABLE 10

5011

Particle size distribution (nm.) Graph of Intensity distribution

| Size range | Graph |
|---|---|
| 16.5–19.9 | + |
| 19.9–24.2 | + |
| 24.2–29.3 | + |
| 29.3–35.5 | + |
| 35.3–43.0 | + |
| 43.0–52.1 | + |
| 52.1–63.1 | + |
| 63.1–76.4 | + |
| 76.4–92.6 | + |
| 92.6–112.1 | + |
| 112.1–135.9 | + |
| 135.9–164.6 | + |
| 164.6–199.4 | |
| 199.4–241.6 | |
| 241.6–292.7 | |
| 292.7–354.6 | |
| 354.6–429.6 | |
| 429.6–520.5 | |
| 520.5–630.6 | |
| 630.6–764.0 | |
| 764.0–925.6 | |
| 925.6–1121.4 | |

TABLE 10-continued

#5011

| Size Class | 1121.4–1358.7 | 1358.7–1646.1 |
|---|---|---|
| | ———————+ | —————+ |

| | % by Intensity | | | % by mass | | | % by number | | |
|---|---|---|---|---|---|---|---|---|---|
| Size Class | Under | In | Above | Under | In | Above | Under | In | Above |
| 16.5–19.9 | 0.0 | 0.0 | 100.0 | 0.0 | 0.0 | 100.0 | 0.0 | 0.0 | 100.0 |
| 19.9–24.2 | 0.0 | 0.0 | 100.0 | 0.0 | 0.0 | 100.0 | 0.0 | 0.0 | 100.0 |
| 24.2–29.3 | 0.0 | 0.0 | 100.0 | 0.0 | 0.0 | 100.0 | 0.0 | 0.0 | 100.0 |
| 29.3–35.3 | 0.0 | 0.0 | 100.0 | 0.0 | 0.0 | 100.0 | 0.0 | 0.0 | 100.0 |
| 35.3–43.0 | 0.0 | 0.0 | 100.0 | 0.0 | 0.0 | 100.0 | 0.0 | 0.0 | 100.0 |
| 43.0–52.1 | 0.0 | 0.0 | 100.0 | 0.0 | 0.0 | 100.0 | 0.0 | 0.0 | 100.0 |
| 52.1–63.1 | 0.0 | 0.0 | 100.0 | 0.0 | 0.0 | 100.0 | 0.0 | 0.0 | 100.0 |
| 63.1–76.4 | 0.0 | 0.0 | 100.0 | 0.0 | 0.0 | 100.0 | 0.0 | 0.0 | 100.0 |
| 76.4–92.6 | 0.0 | 0.0 | 100.0 | 0.0 | 0.0 | 100.0 | 0.0 | 0.0 | 100.0 |
| 92.6–112.1 | 0.0 | 0.0 | 100.0 | 0.0 | 0.0 | 100.0 | 0.0 | 0.0 | 100.0 |
| 112.1–135.9 | 0.0 | 0.0 | 100.0 | 0.0 | 0.0 | 100.0 | 0.0 | 0.0 | 100.0 |
| 135.9–164.6 | 0.0 | 0.0 | 100.0 | 0.0 | 0.0 | 100.0 | 0.0 | 0.0 | 100.0 |
| 164.6–199.4 | 0.0 | 1.7 | 98.3 | 0.0 | 0.1 | 99.9 | 0.0 | 2.5 | 97.5 |
| 199.4–241.6 | 1.7 | 7.7 | 90.6 | 0.1 | 0.3 | 99.5 | 2.5 | 3.4 | 94.1 |
| 241.6–292.7 | 9.4 | 13.2 | 77.4 | 0.5 | 0.5 | 99.1 | 5.9 | 2.9 | 91.3 |
| 292.7–354.6 | 22.6 | 11.1 | 66.3 | 0.9 | 0.6 | 98.4 | 8.7 | 2.1 | 89.2 |
| 354.6–429.6 | 33.7 | 7.9 | 58.4 | 1.6 | 18.8 | 79.7 | 10.8 | 34.9 | 54.3 |
| 429.6–520.5 | 41.8 | 15.2 | 43.2 | 20.3 | 37.1 | 42.5 | 45.7 | 38.8 | 15.5 |
| 520.5–630.6 | 56.8 | 14.9 | 28.4 | 57.5 | 19.7 | 22.8 | 84.5 | 11.6 | 3.9 |
| 630.6–764.0 | 71.6 | 10.9 | 17.5 | 77.2 | 5.1 | 17.7 | 96.1 | 1.7 | 2.2 |
| 764.0–925.6 | 82.5 | 7.4 | 10.0 | 82.3 | 8.2 | 9.5 | 97.8 | 1.5 | 0.7 |
| 925.6–1121.4 | 90.0 | 5.0 | 5.0 | 90.5 | 4.7 | 4.8 | 99.3 | 0.5 | 0.2 |
| 1121.4–1358.7 | 95.0 | 3.2 | 1.8 | 95.2 | 1.9 | 3.0 | 99.8 | 0.1 | 0.1 |
| 1358.7–1646.1 | 98.2 | 1.8 | 0.0 | 97.0 | 3.0 | 0.0 | 99.9 | 0.1 | 0.0 |

TABLE 11

#5012

Particle size distribution (nm.) Graph of Intensity distribution

| | |
|---|---|
| 39.1–47.4 | + |
| 47.4–57.4 | + |
| 57.4–69.6 | + |
| 69.6–84.3 | + |
| 84.3–102.1 | + |
| 102.1–123.7 | + |
| 123.7–149.9 | + |
| 149.9–181.6 | ————————————+ |
| 181.6–220.0 | ——————————————————————————————+ |
| 220.0–266.5 | ——————————————————————————+ |
| 266.5–322.9 | ——————————+ |
| 322.9–391.2 | ———————+ |
| 391.2–473.9 | ———————+ |
| 473.9–574.2 | ——————————————+ |
| 574.2–695.6 | ————————————————————+ |
| 695.6–842.8 | ——————————————————+ |
| 842.8–1021.0 | ————————————————+ |
| 1021.0–1237.0 | ——————————————+ |
| 1237.0–1498.7 | ——————+ |
| 1498.7–1815.7 | ———+ |
| 1815.7–2199.7 | —+ |
| 2199.7–2665.1 | + |
| 2665.1–3228.8 | + |
| 3228.8–3911.8 | + |

| | % by Intensity | | | % by mass | | | % by number | | |
|---|---|---|---|---|---|---|---|---|---|
| Size Class | Under | In | Above | Under | In | Above | Under | In | Above |
| 39.1–47.4 | 0.0 | 0.0 | 100.0 | 0.0 | 0.0 | 100.0 | 0.0 | 0.0 | 100.0 |
| 47.4–57.4 | 0.0 | 0.0 | 100.0 | 0.0 | 0.0 | 100.0 | 0.0 | 0.0 | 100.0 |
| 57.4–69.6 | 0.0 | 0.0 | 100.0 | 0.0 | 0.0 | 100.0 | 0.0 | 0.0 | 100.0 |
| 69.6–84.3 | 0.0 | 0.0 | 100.0 | 0.0 | 0.0 | 100.0 | 0.0 | 0.0 | 100.0 |
| 84.3–102.1 | 0.0 | 0.0 | 100.0 | 0.0 | 0.0 | 100.0 | 0.0 | 0.0 | 100.0 |
| 102.1–123.7 | 0.0 | 0.0 | 100.0 | 0.0 | 0.0 | 100.0 | 0.0 | 0.0 | 100.0 |
| 123.7–149.9 | 0.0 | 0.0 | 100.0 | 0.0 | 0.0 | 100.0 | 0.0 | 0.0 | 100.0 |

TABLE 11-continued

5012

| | | | | | | | | | |
|---|---|---|---|---|---|---|---|---|---|
| 149.9–181.6 | 0.0 | 5.0 | 95.0 | 0.0 | 1.5 | 98.5 | 0.0 | 28.0 | 72.0 |
| 181.6–220.0 | 5.0 | 14.4 | 80.5 | 1.5 | 2.4 | 96.1 | 28.0 | 25.5 | 46.5 |
| 220.0–266.5 | 19.5 | 12.7 | 67.9 | 3.9 | 2.1 | 94.1 | 53.5 | 12.4 | 34.1 |
| 266.5–322.9 | 32.1 | 5.5 | 62.4 | 5.9 | 1.2 | 92.8 | 65.9 | 4.1 | 30.0 |
| 322.9–391.2 | 37.6 | 2.9 | 59.5 | 7.2 | 2.4 | 90.5 | 70.0 | 4.5 | 25.5 |
| 391.2–473.9 | 40.5 | 5.0 | 54.5 | 9.5 | 8.2 | 82.3 | 74.5 | 8.7 | 16.8 |
| 473.9–574.2 | 45.5 | 7.2 | 47.3 | 17.7 | 12.1 | 70.2 | 83.2 | 7.2 | 9.6 |
| 574.2–695.6 | 52.7 | 11.4 | 35.9 | 29.8 | 11.9 | 58.2 | 90.4 | 4.0 | 5.5 |
| 695.6–842.8 | 64.1 | 12.0 | 23.9 | 41.3 | 13.5 | 44.8 | 94.5 | 2.5 | 3.0 |
| 842.8–1021.0 | 76.1 | 9.8 | 14.1 | 55.2 | 15.8 | 29.0 | 97.0 | 1.7 | 1.3 |
| 1021.0–1237.0 | 85.9 | 6.9 | 7.2 | 71.0 | 15.6 | 13.3 | 98.7 | 0.9 | 0.4 |
| 1237.0–1498.7 | 92.8 | 4.3 | 2.9 | 86.7 | 9.1 | 4.2 | 99.6 | 0.3 | 0.1 |
| 1498.7–1815.7 | 97.1 | 2.3 | 0.6 | 95.8 | 3.0 | 1.3 | 99.9 | 0.1 | 0.0 |
| 1815.7–2199.7 | 99.4 | 0.6 | 0.0 | 98.7 | 1.3 | 0.0 | 100.0 | 0.0 | 0.0 |
| 2199.7–2665.1 | 100.0 | 0.0 | 0.0 | 100.0 | 0.0 | 0.0 | 100.0 | 0.0 | 0.0 |
| 2665.1–3228.8 | 100.0 | 0.0 | 0.0 | 100.0 | 0.0 | 0.0 | 100.0 | 0.0 | 0.0 |
| 3228.8–3911.8 | 100.0 | 0.0 | 0.0 | 100.0 | 0.0 | 0.0 | 100.0 | 0.0 | 0.0 |

TABLE 12

5013

Particle size distribution (nm.) Graph of Intensity distribution

| | 39.0–47.3 | + |
| | 47.3–57.3 | + |
| | 57.3–69.4 | + |
| | 69.4–84.1 | + |
| | 84.1–101.9 | + |
| | 101.9–123.4 | + |
| | 123.4–149.5 | + |
| | 149.5–181.2 | + |
| | 181.2–219.5 | + |
| | 219.5–265.9 | + |
| | 265.9–322.1 | + |
| | 322.1–390.3 | + |
| | 390.3–472.8 | + |
| | 472.8–572.9 | |
| | 572.9–694.0 | |
| | 694.0–840.8 | |
| | 840.8–1018.7 | |
| | 1018.7–1234.2 | |
| | 1234.2–1495.3 | |
| | 1495.3–1811.5 | |
| | 1811.5–2194.7 | |
| | 2194.7–2659.0 | |
| | 2659.0–3221.4 | |
| | 3221.4–3902.9 | |

| | % by Intensity | | | % by mass | | | % by number | | |
|---|---|---|---|---|---|---|---|---|---|
| Size Class | Under | In | Above | Under | In | Above | Under | In | Above |
| 39.0–47.3 | 0.0 | 0.0 | 100.0 | 0.0 | 0.0 | 100.0 | 0.0 | 0.0 | 100.0 |
| 57.3–69.4 | 0.0 | 0.0 | 100.0 | 0.0 | 0.0 | 100.0 | 0.0 | 0.0 | 100.0 |
| 69.4–84.1 | 0.0 | 0.0 | 100.0 | 0.0 | 0.0 | 100.0 | 0.0 | 0.0 | 100.0 |
| 84.1–101.9 | 0.0 | 0.0 | 100.0 | 0.0 | 0.0 | 100.0 | 0.0 | 0.0 | 100.0 |
| 101.9–123.4 | 0.0 | 0.0 | 100.0 | 0.0 | 0.0 | 100.0 | 0.0 | 0.0 | 100.0 |
| 123.4–149.5 | 0.0 | 0.0 | 100.0 | 0.0 | 0.0 | 100.0 | 0.0 | 0.0 | 100.0 |
| 1495.–181.2 | 0.0 | 0.0 | 100.0 | 0.0 | 0.0 | 100.0 | 0.0 | 0.0 | 100.0 |
| 181.2–219.5 | 0.0 | 0.0 | 100.0 | 0.0 | 0.0 | 100.0 | 0.0 | 0.0 | 100.0 |
| 219.5–265.9 | 0.0 | 0.0 | 100.0 | 0.0 | 0.0 | 100.0 | 0.0 | 0.0 | 100.0 |
| 265.9–322.1 | 0.0 | 0.0 | 100.0 | 0.0 | 0.0 | 100.0 | 0.0 | 0.0 | 100.0 |
| 322.1–390.3 | 0.0 | 0.0 | 100.0 | 0.0 | 0.0 | 100.0 | 0.0 | 0.0 | 100.0 |
| 390.3–472.8 | 0.0 | 0.0 | 100.0 | 0.0 | 0.0 | 100.0 | 0.0 | 0.0 | 100.0 |
| 472.8–572.9 | 0.0 | 1.5 | 98.5 | 0.0 | 1.3 | 98.7 | 0.0 | 11.6 | 88.4 |
| 572.9–694.0 | 1.5 | 5.7 | 92.8 | 1.3 | 2.5 | 96.2 | 11.6 | 12.7 | 75.7 |
| 694.0–840.8 | 7.2 | 6.5 | 86.3 | 3.8 | 4.3 | 91.9 | 24.3 | 12.3 | 63.4 |
| 840.8–1018.7 | 13.7 | 9.7 | 76.6 | 8.1 | 15.3 | 76.6 | 36.6 | 24.5 | 38.9 |
| 1018.7–1234.2 | 23.4 | 24.9 | 51.6 | 23.4 | 26.9 | 49.7 | 61.1 | 24.3 | 14.6 |
| 1234.2–1495.3 | 48.4 | 20.7 | 30.9 | 50.3 | 19.3 | 30.4 | 84.3 | 9.8 | 4.8 |
| 1495.3–1811.5 | 69.1 | 13.0 | 18.0 | 69.6 | 9.2 | 21.2 | 95.2 | 2.6 | 2.2 |
| 1811.5–2194.7 | 82.0 | 8.2 | 9.7 | 78.8 | 7.8 | 13.4 | 97.8 | 1.3 | 1.0 |
| 2194.7–2659.0 | 90.3 | 5.2 | 4.5 | 86.6 | 7.3 | 6.1 | 99.0 | 0.7 | 0.3 |

TABLE 12-continued

| #5013 | | | | | | | | |
|---|---|---|---|---|---|---|---|---|
| 2659.0–3221.4 | 95.5 | 3.0 | 1.5 | 93.9 | 6.1 | 0.0 | 99.7 | 0.3 | 0.0 |
| 3221.4–3902.9 | 98.5 | 1.5 | 0.0 | 100.0 | 0.0 | 0.0 | 100.0 | 0.0 | 0.0 |

Example
Skin permeation parametersa

| | Formulation (Table 7) | | | Blank (1% Minoxidil in alcohol) |
|---|---|---|---|---|
| | IP2 | IP3 | IP4 | |
| Qrec ($\mu g/cm^2$) | 1230 ± 295 | 1926 ± 616 | 1456 ± 460 | 45.7 ± 13 |
| Qskin ($\mu g/cm^2$) | 310 ± 68 | 426 ± 72 | 410 ± 89 | 38.7 ± 21 |

The ethosomal systems showed an increase of up to 42 times in Qrec and up to 11 times in Qskin.

These results clearly Indicate that the ethosomal system is an effective penetration enhancing system.

References

1. Barry, B. W., Optimizing percutaneous absorption. In Bronaugh, R. L. and Maibach, M. I. (Eds), Percutaneous Absorption, Dekker, New York, 1989, pp. 531–565.

2. Batzri, S. and Korn, E. D. Single bilayer liposomes prepared without sonication. Biochim. Biophys. Acta 298 1973) 1015–1019.

3. Kremer, J. M. H., v. d. Esker, M. W. J., Pathmamanoharan, C. and Wiersema, P. H. Vesicles of variable diameter prepared by a modified injection method. Biochemistry 16 (1977) pp.3932–3935.

4. Leigh, S., Pro-liposome compositions, U.S. Pat. No. 5,004,611, Apr. 2, 1991.

5. Riaz, M., Weiner, N., Martin, F. In Pharmaceutical Dosage Forms. Disperse Systems, Vol. 2; Lieberman, H. A., Rieger, M. M., Banker, G. S., Eds, Marcel Dekker, Inc. New York and Basel, 1988 pp 567–602.

6. Touitou, E. and Fabin, B. Altered skin permeation of a highly lipophilic molecule: tetrahydrocannabinol. Int. J. Pharm. 43 (1988) 17–22.

7. Touitou, E., Levi-Schaffer, F., Shaco-Ezra, N., Ben-Yossef, Ramy and Fabin, B. Enhanced permeation of theophylline through the skin and its effect on fibroblast proliferation. Int. J. Pharm. 70 (1991) 159–166.

I claim:

1. A liposomal composition for topical application to the skin, resulting in enhanced transdermal passage through or introduction of an active ingredient into the skin, which composition comprises from 0.5% to 10% phospholipids, from 5% to 35% of a $C_3$ or $C_4$ alcohol, 15l to 30% ethanol, wherein the combined content of ethanol and $C_3$ or $C_4$ alcohol is at least 20 wt. % and not more than 40 wt. %, up to 20 wt. % glycol, at least 20% water and at least one active ingredient.

2. A composition according to claim 1, where the phospholipids comprise at least one member selected from the group consisting of phosphatidylcholine (P C), hydrogenated P C, phosphatidic acid (P A), phosphatidylserine (P S), phosphatidylethanolamine (P E), phosphatidylglycerol (P P G) and phosphatidylinositol (P I).

3. A composition according to claim 1, where the $C_3$ alcohol is isopropanol and where the glycol is propylene glycol.

4. A composition according to claim 1, wherein the active ingredient is at least one member selected from the group consisting of peptides, enzymes, hormones, anti-aging agents, tanning agents, vitamins, melanin, melatonin, anti-viral drugs, plant extracts, glycosides, alkaloids, anxiolytics, antiepileptics, antifundals, non-steroidal anti-inflammatory drugs, antihypertensive agents, corticosteroids, minoxidil, cannabinoids, antibiotics, hydroxy acids, antimitotics, antimycotics, retinoic acid, diclofenac and acyclovir.

5. A process for the production of a cosmetic or medical composition for topical application to the skin, for rapidly introducing into the skin, or for enhanced penetration through the skin, wherein said process comprises:

mixing from 0.5% to 10% phospholipids, from 5% to 35% of a $C_3$ or $C_4$ alcohol, 15% to 30% ethanol, $C_3$ or $C_4$ alcohol is at least 20 wt. % and not more than 40 wt. %, up to 20 wt. % glycol, at least 20% water and at least one active ingredient, and forming a colloid system containing vesicles.

* * * * *